United States Patent [19]

Coates et al.

[11] Patent Number: 5,075,310

[45] Date of Patent: Dec. 24, 1991

[54] PYRIMIDONE DERIVATIVES AS BRONCHODILATORS

[75] Inventors: William J. Coates, Welwyn Garden City; Derek A. Rawlings, Stevenage, both of England

[73] Assignee: Smith Kline & French Laboratories, Ltd., Welwyn Garden City, England

[21] Appl. No.: 370,494

[22] Filed: Jun. 23, 1989

[30] Foreign Application Priority Data

Jul. 1, 1988 [GB] United Kingdom ................. 8815716
Jul. 1, 1988 [GB] United Kingdom ................. 8815717
Jul. 1, 1988 [GB] United Kingdom ................. 8815718

[51] Int. Cl.$^5$ ................. A61K 31/495; C01D 495/04
[52] U.S. Cl. ................. 514/258; 544/254; 544/262; 544/278
[58] Field of Search ................. 544/254, 262, 278; 514/258

[56] References Cited

U.S. PATENT DOCUMENTS 4,039,544  8/1977  Broughton .................. 544/254
4,885,301 12/1989  Coates ........................ 514/263

FOREIGN PATENT DOCUMENTS 201188 12/1986  European Pat. Off. .
293063 11/1988  European Pat. Off. .
347027 12/1989  European Pat. Off. .
347146 12/1989  European Pat. Off. .
1284084  8/1972  United Kingdom .

OTHER PUBLICATIONS

Chemical Abstracts, vol. 83, No. 15, #131544s.
Broughton et al., "Anti-Allergic Activity of 2--Phenyl-8-azapurin-6-ones", *J. Med. Chem.*, 18, 1117 (1975).
Hamilton et al., "Synthesis and Structure-Activity Relationships of Pyrazolo(4,3-d)pyrimidin-7-ones as Adenosine Receptor Antagonists", J. Med. Chem. 30, 91 (1987).
Baker et al., "Irreversible Enzyme Inhibitors CXXV. Active-Site-Directed Irreversible Inhibitors of Xanthine Oxidase Derived from Arylpurines and Pyrazole . . . Fluoride", J. Med. Chem. 11, 656 (1968).

*Primary Examiner*—Donald G. Daus
*Assistant Examiner*—Jyothsna Venkat
*Attorney, Agent, or Firm*—Charles M. Kinzig; Stuart R. Suter; Edward T. Lentz

[57] ABSTRACT

This invention relates to fused pyrimidine derivatives which have bronchodilator activity. A compound of this invention is 2-(2-propoxyphenyl)thieno[2,3-d]pyrimidin-4(3H)-one.

10 Claims, No Drawings

PYRIMIDONE DERIVATIVES AS BRONCHODILATORS

The present invention relates to fused pyrimidine derivatives, intermediates in their preparation, pharmaceutical compositions containing them and a method of effecting bronchodilatation by administering them. The compounds of this invention are inhibitors of a calmodulin insensitive cyclic GMP phosphodiesterase and are of use in combatting such conditions where such inhibition is thought to be beneficial. They are bronchodilators and are therefore of use in combatting chronic reversible obstructive lung diseases such as asthma and bronchitis. Furthermore the compounds of this invention are vasodilators and are therefore of value in combatting angina, hypertension and congestive heart failure.

Accordingly the present invention provides compounds of the formula (1):

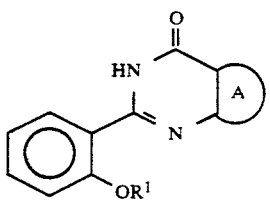

and pharmaceutically acceptable salts thereof, wherein

is a ring of sub-formula (a) (b) or (c):

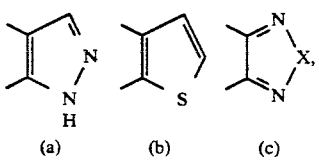

X is oxygen or sulphur, and
$R^1$ is $C_{1-6}$alkyl, $C_{2-6}$alkenyl, $C_{3-5}$cycloalkyl$C_{1-4}$alkyl, or $C_{1-4}$alkyl substituted by 1 to 6 fluoro groups.

Suitably $R^1$ is $C_{2-5}$alkyl for example ethyl, n-propyl, isopropyl, butyl, isobutyl or pentyl.

Suitably $R^1$ is $C_{3-5}$alkenyl for example allyl, butenyl or pentenyl.

Suitably $R^1$ is cyclopropylmethyl.

Examples of $C_{1-4}$alkyl substituted by 1 to 6 fluoro groups include —$CF_3$, —$CH_2CF_3$ or —$CF_2CHFCF_3$.

Preferably $R^1$ is n-propyl.

Suitably

is group of sub-formula (a) thus forming a pyrazolo[3,4-d]pyrimidine ring system.

Suitably

is a group of sub-formula (b) thus forming a thieno[2,3-d]pyrimidine ring system.

Suitably

is a group of sub-formula (c) and X is oxygen thus forming a [1,2,5]oxadiazolo[3,4-d]pyrimidine ring system.

Suitably

is a group of sub-formula (c) and X is sulphur thus forming a [1,2,5]thiadiazolo[3,4-d]pyrimidine ring system.

Particular compounds of this invention are:
6-(2-propoxyphenyl)pyrazolo[3,4-d]pyrimidin-4(5H)-one,
2-(2-propoxyphenyl)thieno[2,3-d]pyrimidin-4(3H)-one,
2-(2-propoxyphenyl)[1,2,5]oxadiazolo[3,4-d]pyrimidin-4(3H)-one, or
2-(2-propoxyphenyl)[1,2,5]thiadiazolo[3,4-d]pyrimidin-4(3H)-one
or pharmaceutically acceptable salts thereof.

This invention covers all tautomeric and optical isomeric forms of compounds of formula (1).

Compounds of the formula (1) may form pharmaceutically acceptable salts with metal ions, such as alkali metals for example sodium and potassium, or with an ammonium ion.

In order to use a compound of the formula (1) or a pharmaceutically acceptable salt thereof for the treatment of humans and other mammals it is normally formulated in accordance with standard pharmaceutical practice as a pharmaceutical composition.

Compounds of formula (1) and their pharmaceutically acceptable salts may be administered in standard manner for the treatment of the indicated diseases, for example orally, sublingually, parenterally, trans-dermally, rectally, via inhalation or via buccal administration.

Compounds of formula (1) and their pharmaceutically acceptable salts which are active when given orally or via buccal administration can be formulated appropriately in dosage forms such as liquids, syrups, tablets, capsules and lozenges. An oral liquid formulation will generally consist of a suspension or solution of the compound or salt in a liquid carrier for example, ethanol, glycerine or water with a flavouring or colouring agent. Where the composition is in the form of a tablet, any pharmaceutical carrier routinely used for preparing solid formulations may be used. Examples of such carriers include starch, celluloses, lactose, sucrose and magnesium stearate. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, or solubilising agent, for example polyethylene glycol, polyvinylpyrrolidone, 2-pyrrolidone, cyclodextrin, lecithin, arachis oil, or sesame oil.

A typical suppository formulation comprises a compound of formula (1) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Typical compositions for inhalation are in the form of a solution, suspension or emulsion that may be administered in the form of an aerosol using a conventional propellant such as dichlorodifluoromethane or trichlorofluoromethane, or are in the form of a powder for insufflation.

Preferably the composition is in unit dosage form, for example a tablet, capsule or metered aerosol dose, so that the patient may administer to himself a single dose.

Each dosage unit for oral administration contains suitably from 0.001 mg/Kg to 30 mg/Kg, and preferably from 0.005 mg/Kg to 15 mg/Kg, and each dosage unit for parenteral administration contains suitably from 0.001 mg/Kg to 10 mg/Kg, of a compound of formula (1) or a pharmaceutically acceptable salt thereof calculated as the free base.

The daily dosage regimen for oral administration is suitably about 0.001 mg/Kg to 120 mg/Kg, of a compound of formula (1) or a pharmaceutically acceptable salt thereof calculated as the free base. The daily dosage regimen for parenteral administration is suitably about 0.001 mg/Kg to 40 mg/Kg, for example about 0.005 mg/Kg to 10 mg/Kg, of a compound of the formula (1) or a pharmaceutically acceptable salt thereof calculated as the free base. The active ingredient may be administered as required for example from 1 to 8 times a day or by infusion. The compositions of the invention are bronchodilators and are useful in chronic reversible obstructive lung disease for example asthma and bronchitis. The compositions of the present invention also have vasodilator activity and are of use in the treatment of angina, hypertension and congestive heart failure. Such conditions can be treated by administration orally, sublingually, topically, rectally, parenterally or by inhalation. For administration by inhalation dosages are controlled by a valve, are administered as required and for an adult are conveniently in the range 0.1-5.0 mg of a compound of the formula (1) or a pharmaceutically acceptable salt thereof.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of the formula (1) are bronchodilators such as sympathomimetic amines for example isoprenaline, isoetharine, sulbutamol, phenylephrine and ephedrine or xanthine derivatives for example theophylline and aminophylline, anti-allergic agents for example disodium cromoglycate, histamine $H_1$-antagonists, vasodilators for example hydralazine, angiotensin converting enzyme inhibitors for example captopril, anti-anginal agents for example isosorbide nitrate, glyceryl trinitrate and pentaerythritol tetranitrate, anti-arrhythmic agents for example quinidine, procainamide and lignocaine, calcium antagonists for example verapamil and nifedipine, diuretics such as thiazides and related compounds for example bendrofluazide, chlorothiazide, chlorothalidone, hydrochlorothiazide, and other diuretics for example frusemide and triamterene, and sedatives for example nitrazepam, flurazepam and diazepam.

The compounds of the formula (1) or pharmaceutically acceptable salts thereof can be prepared by a process which comprises:

a) for compounds wherein

is a group of sub-formula (a), reacting a compound of the formula (2):

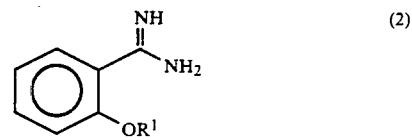

wherein $R^1$ is as hereinbefore defined with a compound of the formula (3):

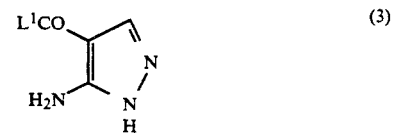

wherein $L^1$ is $C_{1-4}$alkoxy or amino;

b) for compounds wherein

is a group of sub-formula (a) or (b), cyclising a compound of the formula (4):

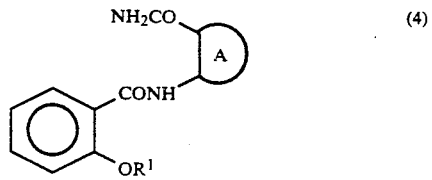

wherein $R^1$ is as hereinbefore defined and

is a group of sub-formula (a) or (b) as hereinbefore defined;
c) for compounds wherein

is a group of sub-formula (c) and X is oxygen, cyclising a compound of the formula (5):

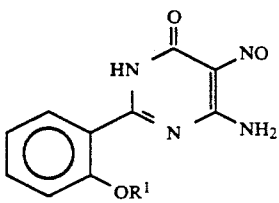

wherein $R^1$ is as hereinbefore defined with an oxidising agent;
d) for compounds wherein

is a group of sub-formula (c) and X is sulphur, reacting a compound of the formula (6):

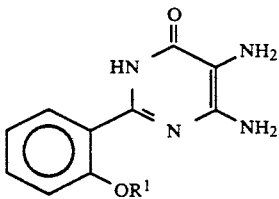

wherein $R^1$ is as hereinbefore defined with thionyl chloride or a chemical equivalent thereof; and thereafter optionally forming a pharmaceutically acceptable salt.

Suitably an acid addition salt of a compound of the formula (2), for example the methanesulphonate or hydrochloride, is reacted with an acid addition salt of a compound of the formula (3), for example the sulphate or hydrochloride, in the presence of a suitable base such as sodium acetate in the absence of a solvent or in a suitable solvent such as a $C_{1-4}$alcohol, pyridine or N-methylpyrrolidin-2-one at an elevated temperature, for example 50°–250° C.

Suitably a compound of the formula (4) is cyclised by heating at an elevated temperature, for example 50°–150° C., in the presence of an acid or a base in a suitable solvent such as aqueous $C_{1-4}$alcohols, water, toluene, a halohydrocarbon or acetonitrile. Conveniently a compound of the formula (4) is cyclised by heating in aqueous base such as sodium hydroxide at the reflux temperature of the reaction mixture.

Suitably a compound of the formula (5) is reacted with an oxidising agent in a solvent such as acetic acid at a moderate temperature e.g. from 0°–80° C., conveniently at ambient temperature. A suitable oxidising agent is lead tetraacetate.

Suitably an acid addition salt of compound of the formula (6), for example the sulphate or hydrochloride, is reacted with excess thionyl chloride or a chemical equivalent thereof in the absence of a solvent or in the presence of a solvent such as a halohydrocarbon at an elevated temperature for example from 50°–200° C., conveniently at the reflux temperature of the reaction mixture. By a chemical equivalent thereof is meant a reagent that will react with a compound of the formula (6) in a similar manner to thionyl chloride to afford a compound of the formula (1) wherein X is sulphur, for example N-thionylaniline (J. Org. Chem., 29, 2135 (1964).

The compounds of the formulae (2), (5) and (6) and acid addition salts thereof are known or preparable in conventional manner from U.S. Pat. No. 3,819,631.

A compound of the formula (4) can be prepared by reaction of 3-amino-4-pyrazolecarboxamide or 2-aminothiophene-3-carboxamide with a compound of the formula (7):

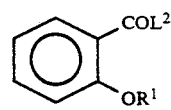

wherein $R^1$ is as hereinbefore defined and $L^2$ is halo.

Suitably $L^2$ is chloro or bromo. Suitably a compound of the formula (7) is reacted with 3-amino-4-pyrazolecarboxamide at ambient or elevated temperature e.g. 50°–100° C. in a suitable solvent such as toluene, acetonitrile or a halohydrocarbon e.g. chloroform or dichloromethane, optionally in the presence of a base such as pyridine or triethylamine, to form a compound of the formula (4) which may be cyclised in situ or may be isolated and thereafter cyclised as hereinbefore described.

Pharmaceutically acceptable base addition salts of the compounds of the formula (1) may be prepared by standard methods, for example by reacting a solution of the compound of the formula (1) with a solution of the base.

The following biological test method, data and Examples serve to illustrate this invention.

Bronchodilatation—In vivo

Male guinea-pigs of the Dunkin Hartley strain (500–600 g) were anaesthetised with Sagatal (pentobarbital sodium) (60 mg/kg). Airway resistance was measured using a modification of the classical Konzett-Rossler technique (J. Pharm. Methods, 13, 309–315, 1985). U46619 (9,11-methanoepoxy-PGH$_2$) was infused i.v. at a rate of 2.5 nmol/min, this produced a steady state of bronchoconstriction (approximately 120% increase from basal airway resistance). The compound under test was administered by i.v. bolus injection, and the subsequent peak inhibition of bronchoconstriction recorded.

The dose of compound required to reduce the U46619-induced bronchoconstriction by 50% is given as the BD$_{50}$. This result demonstrates in vivo anti-bronchoconstrictor activity.

| Compound of Example | BD$_{50}$ (μmol/kg) |
| --- | --- |
| 1 | 5.13 |
| 2 | 2.62 |
| 4 | 4.51 |

EXAMPLE 1

6-(2-Propoxyphenyl)pyrazolo[3,4-d]pyrimidin-4(5H)-one

A stirred mixture of 2-propoxybenzamidine methanesulphonate (1.0 g), 3-amino-4-pyrazolecarboxamide sulphate (0.5 g) and sodium acetate (0.82 g) was heated in an oil bath (180° C.) for one hour. The reaction mixture was dissolved in hot 2 Normal sodium hydroxide (10 ml) and the solution was treated with charcoal and neutralised with glacial acetic acid. A precipitate was collected, washed with water and eluted from a silica column with chloroform. The combined fractions containing product were evaporated to dryness to afford the title compound, 148 mg, m.p. 182°–183.5° C.

EXAMPLE 2

2-(2-Propoxyphenyl)thieno[2,3-d]pyrimidin-4(3H)-one a) A solution of 2-propoxybenzoyl chloride (0.99 g) in acetonitrile (7.5 ml) was added dropwise over 5 minutes to a cooled (0° C.), stirred mixture of 2-aminothiophene-3-carboxamide (0.71 g) and triethylamine (0.51 g) in acetonitrile (7.5 ml). The reaction mixture was stirred for one hour while being allowed to warm to ambient temperature and was then allowed to stand overnight. Acetonitrile was removed under reduced pressure and the residue was washed with water and recrystallised from ethanol-water to afford 2-(2-propoxybenzamido)-thiophene-3-carboxamide, 0.91 g, m.p. 176.5°–178.5° C.

b) A stirred mixture of 2-(propoxybenzamido)-thiophene-3-carboxamide (0.90 g) and pyridine (1 ml) in 2 Normal sodium hydroxide (25 ml) was heated under reflux for 2 hours. The cooled reaction mixture was neutralised with concentrated hydrochloric acid to afford a precipitate and the resulting mixture was extracted with chloroform (3×25 ml). The combined extracts were washed with water (20 ml) and brine (20 ml), dried (magnesium sulphate) and evaporated under reduced pressure to afford a crude product which was recrystallised from ethanol-water to afford the title compound, 0.41 g, m.p. 115°–117° C.

EXAMPLE 3

2-(2-Propoxyphenyl)[1,2,5]oxadiazolo[3,4-d]pyrimidin-4(3H)-one

Lead tetraacetate (1 g) was added portionwise over 5 minutes to a stirred solution of 4-amino-5-nitroso-2-(2-propoxyphenyl)pyrimidin-6-one (0.52 g) in acetic acid (10 ml) under nitrogen. The reaction mixture was stirred for 1.5 hours and then allowed to stand overnight. A precipitate was collected, washed with water, dissolved in hot methanol and treated with charcoal. The methanolic solution was filtered through diatomaceous earth and the filtrate was evaporated under reduced pressure to afford a residue which was recrystallised from methanol to afford the title compound, 0.19 g, m.p. 163°–164° C.

EXAMPLE 4

2-(2-Propoxyphenyl)[1,2,5]thiadiazolo[3,4-d]pyrimidin-4(3H)-one

A stirred solution of 4,5-diamino-2-(2-propoxyphenyl)-pyrimidin-6-one sulphate (0.72 g) in thionyl chloride (25 ml) was heated under reflux for 2 hours. The cooled reaction mixture was evaporated under reduced pressure and the residue was washed with water and recrystallised from methanol-water and then from methanol to afford the title compound, 0.38 g, m.p. 157.5°–158.5° C.

EXAMPLE 5

Pharmaceutical compositions for oral administration are prepared by combining the following:

|  | % w/w | | |
| --- | --- | --- | --- |
| 2-(2-Propoxyphenyl)thieno[2,3-d]pyrimidin-4(3H)-one | 0.5 | 3.0 | 7.14 |
| 2% w/w Soya lecithin in soya bean oil | 90.45 | 88.2 | 84.41 |
| Hydrogenated vegetable shortening and beeswax | 9.05 | 8.8 | 8.45 |

The formulations are then filled into individual soft gelatin capsules.

EXAMPLE 6

A pharmaceutical composition for parenteral administration is prepared by dissolving the title compound of Example 4 (0.02 g) in polyethylene glycol 300 (25 ml) with heating. This solution is then diluted with water for injections Ph. Eur. (to 100 ml). The solution is then sterilised by filtration through a 0.22 micron membrane filter and sealed in sterile containers.

What is claimed is:

1. A compound of the formula (1):

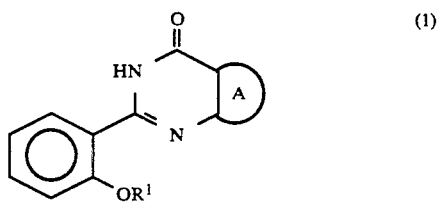

or a pharmaceutically acceptable salt thereof, wherein

is a ring of sub-formula (a), (b) or (c):

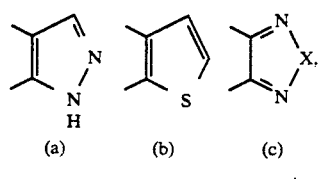

X is oxygen or sulphur, and
R$^1$ is C$_{1-6}$alkyl, C$_{2-6}$alkenyl, C$_{3-5}$cycloalkylC$_{1-4}$alkyl, or C$_{1-4}$alkyl substituted by 1 to 6 fluoro groups.

2. A compound according to claim 1 wherein $R^1$ is $C_{2-5}$alkyl.

3. A compound according to claim 2 wherein $R^1$ is n-propyl.

4. A compound according to claim 1 where

is a group of sub-formula (a).

5. A compound according to claim 1 where

is a group of sub-formula (b).

6. A compound according to claim 1 where

is a group of sub-formula (c) and X is oxygen.

7. A compound according to claim 1 where

is a group of sub-formula (c) and X is sulphur.

8. A compound according to claim 1 which is selected from the group consisting of:
6-(2-propoxyphenyl)pyrazolo[3,4-d]pyrimidin-4(5H)-one,
2-(2-propoxyphenyl)thieno[2,3-d]pyrimidin-4(3H)-one,
2-(2-propoxyphenyl)[1,2,5]oxadiazolo[3,4-d]pyrimidin-4(3H)-one, or
2-(2-propoxyphenyl)[1,2,5]thiadiazolo[3,4-d]pyrimidin-4(3H)-one,
or a pharmaceutically acceptable salt thereof.

9. A pharmaceutical composition for effecting bronchodilatation which comprises a compound according to claim 1 and a pharmaceutically acceptable carrier.

10. A method of effecting bronchodilation in a host in need thereof by administration of a non-toxic but effective amount of a compound according to claim 1.

* * * * *